United States Patent [19]

Skidmore

[11] Patent Number: 5,507,295
[45] Date of Patent: Apr. 16, 1996

[54] MEDICAL DEVICES

[75] Inventor: Robert Skidmore, Bristol, England

[73] Assignee: British Technology Group Limited, London, England

[21] Appl. No.: 335,889

[22] PCT Filed: Jun. 29, 1993

[86] PCT No.: PCT/GB93/01359

§ 371 Date: Nov. 17, 1994

§ 102(e) Date: Nov. 17, 1994

[87] PCT Pub. No.: WO94/01037

PCT Pub. Date: Jan. 20, 1994

[30] Foreign Application Priority Data

Jul. 1, 1992 [GB] United Kingdom ............... 9213978

[51] Int. Cl.[6] ............................................. A61B 8/12
[52] U.S. Cl. ............................... 128/662.06; 600/121
[58] Field of Search ................... 128/660.09, 660.10, 128/661.08, 661.09, 661.10, 662.01, 662.03, 662.04, 662.06; 600/121, 122, 123, 124, 125

[56] References Cited

U.S. PATENT DOCUMENTS

| 4,593,699 | 6/1986 | Poncy et al. . | |
| 4,815,470 | 3/1989 | Curtis et al. | 128/662.03 |
| 5,205,292 | 4/1993 | Czar et al. | 128/662.03 |
| 5,289,821 | 3/1994 | Swartz | 128/662.03 |

FOREIGN PATENT DOCUMENTS

| 0217689 | 4/1987 | European Pat. Off. . |
| 0246176 | 11/1987 | European Pat. Off. . |
| WO90/2519 | 3/1990 | WIPO . |

OTHER PUBLICATIONS

D. Laughlin et al. "New construction methods for a family of doppler transducers". Proc. of the 7th Ann. Conf. of the IEEE/EMB Society, 27 Sep. 1985, Chicago, Ill. US pp. 231–236.

Primary Examiner—George Manuel
Attorney, Agent, or Firm—Nixon & Vanderhye

[57] ABSTRACT

The present invention relates to a device to allow access of a medical sensor probe to a selected location within a patient's body. A disposable elongated tubular sheath (2) is releasably attached at its closed distal end (10) to the wall of a blood vessel (1) during surgery. The sheath leads out of the patient's body and provides an access path through which a sensor probe, such as an ultrasound probe (3), can be introduced in order to allow monitoring of blood flow within the vessel. The probe can be easily removed and replaced without contamination. When monitoring is complete, the releasable attachment means are operated and the sheath can be pulled out of the patient's body without further surgery.

10 Claims, 1 Drawing Sheet

MEDICAL DEVICES

BACKGROUND OF THE INVENTION

The use of implantable probes or sensors to monitor the operation of organs within the human body has become considerably more common in recent years and, in particular, the continuous post-operative measurement of blood flow in vessels is frequently required in order to evaluate the results of medical procedures. A common and convenient type of probe for this purpose is of ultrasound Doppler form, such a probe being used as a blood flow velocity sensor. In the case of heart operations the ability to monitor post-operatively cardiac performance is required and this can be done by measuring the blood volume flow through the ascending aorta. The probe is located adjacent to the aorta during cardiac surgery and can be connected to monitoring equipment in the operating theatre. Subsequent to the operation the connecting leads can be unplugged and the patient moved to, say, an intensive care unit where similar monitoring equipment is available. The probe can then be connected again for continued monitoring over the required period of investigation.

To achieve accurate flow velocity measurements the Doppler probe must be attached firmly to the vessel under investigation. This is to ensure correct orientation of the probe and to ensure that the probe is not free to move relative to the wall of the vessel. However, in order to avoid a further operation to remove the probe from the vessel the probe must be extractable from outside the body of the patient without causing damage to the vessel or to the surrounding tissue. Known methods proposed for attaching the probe include suturing it to the vessel, or embedding a part of the probe directly in the vessel wall. The non-surgical removal is subsequently achieved by pulling the leads connected to the probe in order to withdraw it from the vessel and from the patient's body. Such removal can clearly be traumatic to the vessel and, because the probe is likely to present an irregular surface, damage can also be caused to other internal organs as it is withdrawn.

An implantable Doppler probe which is removable after use through a small opening in the patient's chest is described in WO-90/02519. The probe can be attached adjacent to the vessel or body under investigation by means of a suturing release feature.

The probe used for such medical purpose is naturally required to be completely sterile and this presents a number of problems, with no guarantee of complete sterility unless autoclaving used. Common practice is to discard the probe after removal and indeed in some jurisdictions it is illegal to reuse such a probe even if effective sterilisation is possible. As a disposable item the probes used are very expensive items due to the fact that they are largely handmade.

An accessory for an ultrasonic diagnostic probe is described in U.S. Pat. No. 4,593,699. As taught in this document, the probe and its connecting cable are sheathed in a removable sterile sleeve to obviate the need for sterilisation of the probe between uses. However, the operation of applying the sleeve to, or removing it from, the probe body must be carried out outside the patient's body.

SUMMARY OF THE INVENTION

It is an object of the present invention to provide a solution to the above-mentioned problems and to this end there is provided a device to allow access of a medical sensor probe to a selected location within a patient's body comprising an elongated tubular sheath having a first portion and a second portion, the two portions to be positioned respectively inside and outside the patient's body, the sheath being closed to the exterior except for at least one opening in the second portion to allow access and removal of the medical sensor probe therethrough, and the first portion having an internal form adapted to accommodate a probe of predetermined shape in a prescribed orientation in the sheath, and having releasable attachment means for securing the sheath at said selected location.

Using this device the releasable attachment means is employed to attach the sheath at the selected location during surgery or otherwise.

In the case of monitoring blood flow in a blood vessel the selected location is the wall of the blood vessel. For this application, it is preferred that the first portion of the sheath has a distal end portion provided with a partially concave external surface to fit against the blood vessel wall.

Using the above-described device, the sensor probe (which, in the case of blood flow monitoring, is likely to be a Doppler ultrasound probe) is inserted into the sheath via the opening in the second portion and thereby located adjacent the vessel. Correctly locating the sensor probe is facilitated by providing the sheath with an internal form adapted to accommodate a probe of predetermined shape.

Preferably, the releasable attachment means is adapted to be operable from outside the patient's body. When monitoring is complete, the probe is removed from the sheath via the opening and the releasable attachment means is operated from outside the patient's body. This terminates the attachment between sheath and vessel and allows the sheath to be withdrawn from the patient's body. In most cases, the sheath can then be discarded.

Because the interior of the sheath is open to the exterior only at an opening outside the patient's body, the artificial barrier provided by the wall of the tubular sheath allows no opportunity for contamination of the probe from the patient during use. The probe can therefore be reused with a sterilised sheath in another patient.

In a preferred form, the releasable attachment means comprises fixing means securable to the selected location, and a tractable element cooperable with the fixing means, the tractable element being guidable in use by guide means associated with the sheath.

By pulling on the tractable element the latter is retraced through the guide means to release the fixing means and thereby release the sheath from the selected location.

In a preferred form of releasable attachment means, the fixing means comprises one or more sutures, the guide means is a bore within the wall of the sheath and the tractable element is a wire.

To prevent reuse of the sheath it can include 'tamper-indicating' means for indicating whether or not the releasable attachment means has been operated. An operator will Know to discard a sheath where the indicator shows it has already been used or tampered with.

BRIEF DESCRIPTION OF THE DRAWINGS

Specific example

An embodiment of the invention will now be described by way of example with reference to the accompanying drawings, in which:

In FIG. 1 a sensor probe 3 Is shown in use in attachment to the wall of a blood vessel 1, such as the ascending aorta. The probe 3 comprises one or more ultrasound transducers 4 fixed at the end of an elongated flexible probe lead body 9 through which the conductor leads 11 pass, these leads being capable of transmitting electrical signals to and from the transducers. In FIG. 1 two transducers 4 are shown, fixed at 45° to the longitudinal direction of the probe, although other orientations and arrangements of transducers are of course possible. The probe 3 is itself located In an extractable manner within a flexible elongated tubular sheath 2, which is closed at its distal end 10, that is, the end to be inserted into the patient's body.

The tubular sheath 2 is to be firmly attached to vessel 1 by appropriate means such as will be described below, and allows the probe 3 to be introduced without having to attach the probe directly to the vessel 1.

Figure 1:
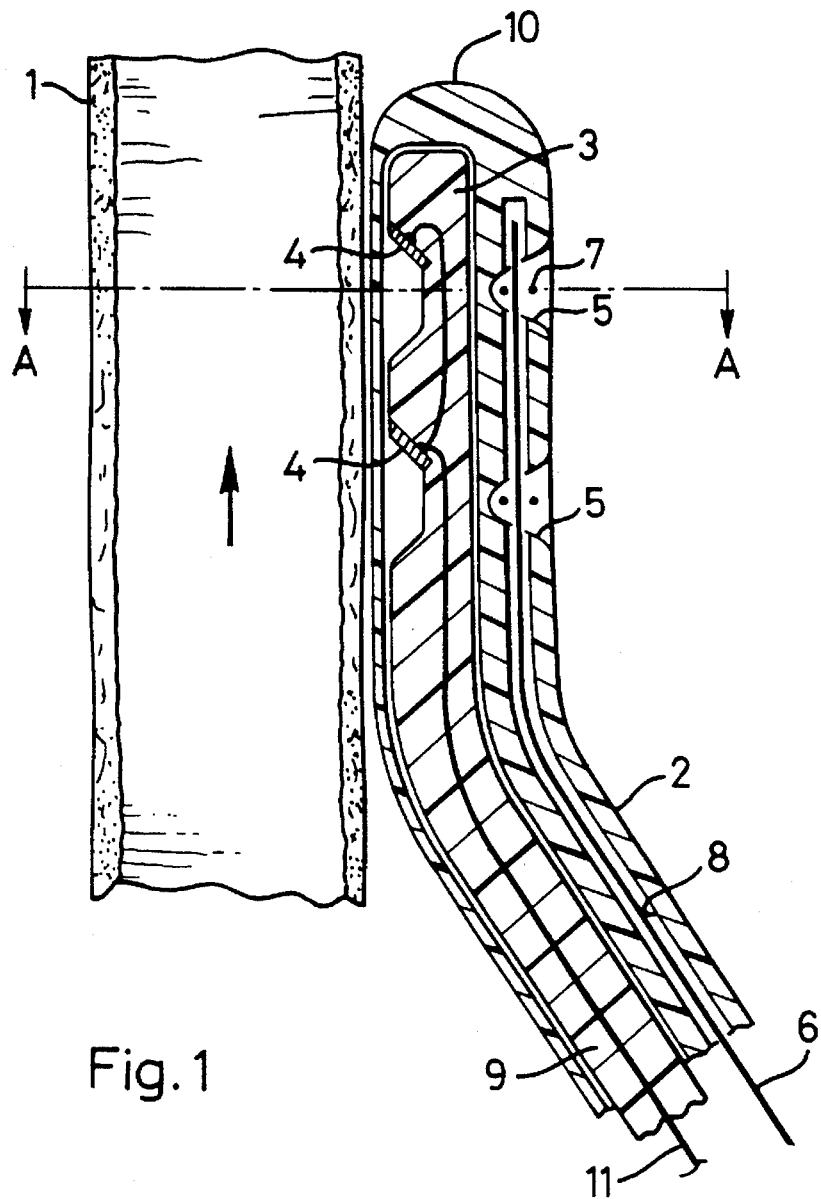
FIG. 1 illustrates a longitudinal section of one embodiment of the device according to the present invention.
Figure 2:
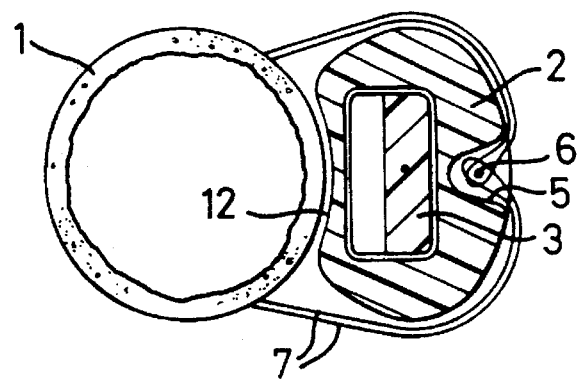
FIG. 2 illustrates a transverse section through the device.

A cross-section taken across the plane represented by line A—A in FIG. 1 is illustrated in FIG. 2, in which it can be seen that the external transverse profile of tubular sheath 2 is of curved form over at least its distal end portion. In this region one side 12 of the tubular sheath has a concave shaping to enable it to fit more snugly against the exterior wall of vessel 1. In section, probe 3 is also of substantially flattened form, such as a broadly rectangular section as shown in FIG. 2, so that it is held in a known, fixed orientation when located within the tubular sheath, this being appropriate to achieve accurate monitoring of the blood flow in the vessel.

The tubular sheath 2 is attached to the vessel by means of a releasable attachment device, the sheath being aligned with the longitudinal direction of the vessel. The releasable attachment device comprises a longitudinal guide bore 8, a number of spaced recesses 5, a stainless steel wire 6 and one or more sutures 7. The guide bore 8 is a blind bore of circular cross-section located within the wall of the sheath on the side of the sheath away from that 12 which fits against the wall of the vessel. The guide bore 8 runs along almost the full length of the tubular sheath, terminating near its distal end and open at its proximal end to allow access by an operator. A number of longitudinally spaced, roughly hemispherical recesses 5 are provided along the length of the wall of the tubular sheath 2 in its distal end portion, the recesses intersecting the guide bore 8. In this way, sections of the guide bore 8 directly link the recesses 5 such that a continuous channel Is provided along the length of tubular sheath 2 open to the exterior only outside the parent's body and where it meets the recesses. There is therefore no possibility of contamination between the interior of guide bore 8 and that of tubular sheath 2, and hence between the interior and the exterior of tubular sheath 2.

In the case of post-operative monitoring of the blood flow in the ascending aorta, access is gained to the aorta during cardiac surgery. The closed distal end 10 of the tubular sheath 2 is introduced into the patient's body with a sterile stainless steel wire 6 in place within the guide bore 8. The surgeon then attaches the tubular sheath to the aorta with sutures 7 which loop around the wire 6 and attach to the vessel walls as shown in FIG. 2. In this illustrated example, two sutures are used at each of the two attachment points corresponding to the two recesses 5, each of the two sutures being attached to opposite sides of the vessel wall. This provides a suitably stable attachment of the tubular sheath to the vessel, but any number of recesses is possible. A single recess may be used but this is less likely to be satisfactory in maintaining the probe 3 in a stable position relative to the vessel 1.

As an alternative, the sutures may be looped around both the wire 6 and the vessel 1, drawn tight and tied.

The external profile of the tubular sheath ensures that it fits very closely against the exterior wall of the aorta 1. The probe 3 may already be in place within the tubular sheath 2, or alternatively the space within the tubular sheath may be initially taken up with a flexible integral filler element (not shown) approximating the size and shape of the probe 3, this filler element being withdrawn once the tubular sheath 2 is attached to the vessel 1 whereupon the probe 3 is introduced by carefully pushing it as far as possible into the tubular sheath from the open proximal end. The patient's chest is then closed leaving the open end of the tubular sheath emerging from the patient's body through an opening in the skin. If necessary, during use, any volume unoccupied by the probe in the interior of tubular sheath 2 may be filled with a saline solution or sound conducting jelly to improve the acoustic coupling and thus aid the ultrasound operation. The sensor leads 11 emerging from the open end of the tubular sheath 2 can then be plugged into monitoring equipment (not shown).

The tubular sheath is then indwelling for the required period, during which time it is possible to remove probe 3, for example for replacement with another sensor, without disturbance to the patient. This is done simply by gentle traction on the flexible probe lead body 9 or on leads 11 which will cause the probe 3 to be withdrawn through the tubular sheath 2. When monitoring is no longer required the probe is withdrawn from the tubular sheath for the last time. Since there has been at no time been any contact between the patient's interior and the probe, the two being separated at all times by the artificial barrier provided by the wall of tubular sheath 2, the probe may simply be set aside to be reused at a later time. Indeed the probe need not even be sterilised between uses.

When the probe has been extracted the releasable attachment device is utilised. Gentle traction is exerted on the stainless steel wire 6, which is withdrawn along guide bore 8, As the end of the wire passes through recesses 5 the loops of sutures 7 are released, and as a result the attachment between tubular sheath 2 and vessel 1 is terminated. The tubular sheath 2 is then free to be gently pulled out through the opening in the patient's skin and can then be discarded. Due to its shape the flexible sheath presents a smooth outer surface and, because of this, its withdrawal is unlikely to cause any damage to the patient. The sutures 7 are of the dissolving type so can simply be left to dissolve within the body over time.

The tubular sheath can also feature a means for indicating whether or not the releasable attachment means has been operated, in order to prevent reuse. This can take the form of a pull-tab (not shown) concealing the tractable end of wire 6 where it emerges from the proximal end of the sheath 2. When the time comes to release the sheath from the vessel, the pull-tab is operated and the end of the wire is thereby revealed, permitting an operator to pull it. The absence of the pull-tab, thereafter indicates that the sheath has been used and should be discarded.

For use, the sheath Is provided in a sterile package to maintain its sterile condition until the package is opened.

Tubular sheath 2 is manufactured by, for example, an extrusion or moulding process, out of a strong, flexible, biologically inert material such as polyurethane or silicon rubber. The sheath is sized for the vessel under investigation, different sized sheaths being selected for different arteries. Such a sheath can be manufactured at a fraction of the cost of a sensor probe and therefore discarding the tubular sheath after each use is a considerably less expensive alternative to discarding the probe itself.

The invention is illustrated with reference to the use of one or more Doppler ultrasound sensors for measuring blood flow velocity, but it is within the scope of the invention to use other types of sensor within the tubular sheath 2, such as, for example, temperature probes. Indeed a multiple sensor probe can be employed in which two or more types of medical sensor are positioned together within the tubular sheath.

Whilst the invention has been described with reference to the illustrated embodiment it is to be understood that the invention is intended to embrace all other embodiments that fall within the spirit and scope of the appended claims.

I claim:

1. A device for allowing access of a medical sensor probe to a selected perivascular location within a patient's body, comprising:

an elongated tubular sheath having a first portion and a second portion, the two portions to be positioned respectively inside and outside the patient's body, said first portion being shaped to fit against a blood vessel wall;

a tubular passageway extending through said sheath, said passageway being closed to the exterior in the first portion and having an opening in the second portion to allow access and removal of a medical sensor probe therethrough whilst said sheath remains indwelling within the patient's body, said closed passageway in said first portion preventing any contact between the patient's interior and said probe; and attachment means located on said first portion for securing said sheath at said selected perivascular location.

2. A device according to claim 1, wherein said first portion of said sheath has a distal end portion provided with a partially concave external surface to fit against the blood vessel wall.

3. A device according to claim 1, wherein said attachment means is releasable by operation from outside the patient's body.

4. A device according to claim 3, wherein said releasable attachment means comprises fixing means securable to the selected location, and a tractable element co-operable with said fixing means, said tractable element being guidable in use by guide means associated with said sheath.

5. A device according to claim 4, wherein said fixing means comprises one or more sutures, said guide means is a bore within a wall of said sheath and said tractable element is a wire.

6. A device according to claim 3 comprising tamper-indicating means for indicating whether or not said releasable attachment means has been operated.

7. A device for allowing access of a medical sensor probe to a selected location within a patient's body, comprising:

an elongated tubular sheath having a first portion and a second portion, the two portions to be positioned respectively inside and outside the patient's body;

a tubular passageway extending through said sheath, said passageway being closed to the exterior in said first portion and having an opening in said second portion to allow access and removal of a medical sensor probe therethrough whilst said sheath remains indwelling within the patient's body, said closed passageway in said first pro%ion preventing any contact between the patient's interior and said probe, said first portion having an internal form for accommodating a probe of predetermined shape in a prescribed orientation in said sheath; and attachment means located on said first portion for securing said sheath at said selected location.

8. A device according to claim 7, wherein said tubular passageway is non-circular.

9. A medical sensor probe kit, comprising:

a Doppler ultrasound probe; and at least one elongated tubular sheath for allowing access of said probe to a selected perivascular location within a patient's body, said sheath having a first portion and a second portion, the two portions to be positioned respectively inside and outside the patient's body, said sheath having a tubular passageway extending therethrough, closed to the exterior in the first portion and having an opening in said second portion to allow access and removal of said probe therethrough whilst said sheath remains indwelling within the patient's body, said first portion of said sheath preventing any contact between the patient's interior and said probe, said first portion being shaped to fit against a blood vessel wall and having attachment means for securing said sheath at said selected perivascular location.

10. A method for locating a medical sensor probe to position said probe at a selected perivascular location within a patient's body, said method comprising:

positioning an elongated tubular sheath against a blood vessel wall, said sheath having a first portion and a second portion, said first portion being positioned inside the patient's body and said second portion being positioned outside the patient's body, said sheath having a tubular passageway extending therethrough, said passageway being closed to the exterior in the first portion and having an opening in the second portion for allowing access and removal of a medical sensor probe therethrough whilst the sheath remains indwelling within the patient's body, the first portion preventing any contact between the patient's interior and the probe, the sheath having attachment means located on said the first portion for securing the sheath at the selected perivascular location;

attaching the tubular sheath to the vessel via the attachment means; and inserting a medical probe into the tubular sheath to position the probe at the selected perivascular location.

* * * * *